United States Patent [19]

Kosaka

[11] Patent Number: 5,457,526
[45] Date of Patent: Oct. 10, 1995

[54] APPARATUS FOR ANALYZING PARTICLES IN FLUID SAMPLES

[75] Inventor: Tokihiro Kosaka, Kakogawashi, Japan

[73] Assignee: Toa Medical Electronics Co., Ltd., Kobe, Japan

[21] Appl. No.: 102,239

[22] Filed: Aug. 5, 1993

[30] Foreign Application Priority Data

Aug. 10, 1992 [JP] Japan .................... 4-235426

[51] Int. Cl.[6] ............................. G01N 15/14; G06K 9/20
[52] U.S. Cl. ................... 356/72; 356/73; 356/39; 250/461.2
[58] Field of Search ................... 356/23, 24, 39, 356/72, 73; 250/461.2

[56] References Cited

U.S. PATENT DOCUMENTS

5,159,397  10/1992  Kosaka et al. .................... 356/73
5,303,027   4/1994  Kuderer et al. .................... 356/328

Primary Examiner—Vincent P. McGraw
Attorney, Agent, or Firm—Jones, Tullar & Cooper

[57] ABSTRACT

An apparatus for analyzing particles capable of obtaining the morphological information or absorption information of particles such as cells in a liquid sample or particles moving in a fluid in real time. As a photo detector, a photo sensor array comprising photo detecting elements (photo sensors) in a row is used, and detection signal groups delivered parallel from the elements (photo sensors) are processed in parallel in a signal processing device, thereby obtaining characteristic parameters of particles moving at high speed, concerning morphology, light absorption (extinction) or the like, in real time.

48 Claims, 10 Drawing Sheets

APPARATUS FOR ANALYZING PARTICLES IN FLUID SAMPLES

CROSS REFERENCE TO RELATED APPLICATION

This application relates to the subject matter of co-pending application, Ser. No. 07/937,340, filed Aug. 31, 1992.

BACKGROUND OF THE INVENTION

The invention relates to an apparatus for analyzing particles such as cells contained in liquid samples of blood, urine and the like, or particles moving in a gas, and more specifically, for example, to an apparatus for analyzing particles capable of obtaining morphological information or light absorption information of individual particles in real time, by illuminating particles such as cells, with light and focusing the transmitted light images on a photo detector in which photo detecting elements are arranged in lines.

By attaching (adding) such apparatus to, for example, a conventional flow cytometer, particles can be judged at higher precision, resulting in an apparatus for analyzing particles of higher reliability.

An apparatus designed to obtain more specific morphological information for individual particles by optically scanning a laser beam reduced narrowly to the particles flowing in the sheath flow in a direction intersecting the flow direction of particles, and obtaining optical signals from parts of particles to be analyzed is known. Herein, the sheath flow refers to a flow having the surroundings of a suspension of particles covered with a sheath liquid of laminar flow in order to pass particles by arranging them in a row precisely in the middle part of the flow.

As the apparatuses for analyzing by extracting the features of particles moving in a fluid flow cytometer and cell sorter are known.

The Japanese Patent Publication Hei. 3-52573 (corresponding to U.S. Pat. No. 4,338,024) discloses an apparatus for forming a flat sheath flow and picking up particle images.

In the conventional flow cytometer, morphological information of particles (area, circumference length, etc.) could not be obtained. Besides, by processing particle images picked up by a video camera, in order to obtain the light absorption (extinction) quantity of each particle and morphological information in real time, an expensive video camera, and a high-performance and expensive exclusive image processor were needed. Moreover, because of the mechanism of picking up by emitting strobe light at specific intervals in one frame period (1/30 sec) of the video camera, particles of low concentration could not be completely captured on the pickup screen of the video camera efficiently, and there were problems in the specimen processing capacity and repeatability of analysis results.

Many proposals have been already disclosed about the apparatus for analyzing flowing particles by scanning a narrowly reduced light beams at high speed, but nothing has been clearly disclosed about how to process optical signals obtained by scanning light beams to obtain morphological information of particles, and how to determine the information in real time every time a particle passes the detecting unit.

The present applicant has already developed an apparatus for analyzing particles capable of determining the morphological information and light absorption quantity of individual particles in real time by adding a detecting system by line sensor (one-dimensional image sensor) and its signal processing system, and scanning the images of particles flowing in a flat sheath flow cell, and applied for patents (Japanese Patent Applications Hei. 3-270106, Hei. 3-270107). However, the sample flow velocity in this apparatus cannot be raised sufficiently because of the relation with the scan cycle time of line sensor and image resolution in the particle flow direction, and the maximum speed was 100 mm/sec, which was about 1/50 that of the conventional flow cytometer. If the sample flow is a flat flow of 100 to 200 µm in width, the analysis quantity per unit time is only 1/5 to 1/10.

In order to increase the number of particles to be analyzed, there is known a method of decreasing the sample dilution factor (raising the particle concentration), and heightening the concentration of particles contained in the sample flow, but the problem is not solved if the sample itself is low in particle density, such as urine samples, or enough sample volume is not obtained.

Besides, when the sample flow is transformed to a flat flow, the probability is high that two or more particles may pass the detecting area of the line sensor simultaneously, which means that plural sets of calculators are needed for obtaining various morphological information or light absorption quantity, and moreover processing the region division is complicated in order to discriminate the individual particles passing very closely to each other.

Thus, in the conventional line sensor (one-dimensional image sensor), since the output signals from the elements were produced in series, particles could not be passed at high speed, and the particle images were blurry, and hence it took a long time in signal processing, too.

OBJECT AND SUMMARY OF THE INVENTION

The present invention is devised in the light of the above problems, and it is hence a primary object thereof to provide an apparatus for analyzing particles capable of obtaining characteristic parameters of particles moving at high speed, regarding morphology, light absorption (extinction) and the like of the particles in real time.

To achieve the above object, in the present invention, the photo detector is a photo sensor array having tiny photo detector elements (photo sensors) arranged in a row, and by parallel signal processing of detection signal groups delivered in parallel from the elements by a signal processor, characteristic parameters regarding morphology, light absorption (extinction) and others of particles moving at high speed can be obtained in real time.

That is, in the present invention, by using the photo sensor array in which detection signals are delivered in parallel from photo sensors, as the means for obtaining the morphological information and light absorption quantity of moving particles, and by parallel processing of the detected signals, the above-mentioned parameters can be obtained in real time if the speed of the moving particles is as fast as several meters/sec, and therefore the number of particles analyzed per unit time can be raised to the level equivalent to the conventional flow cytometer.

Figure 1:
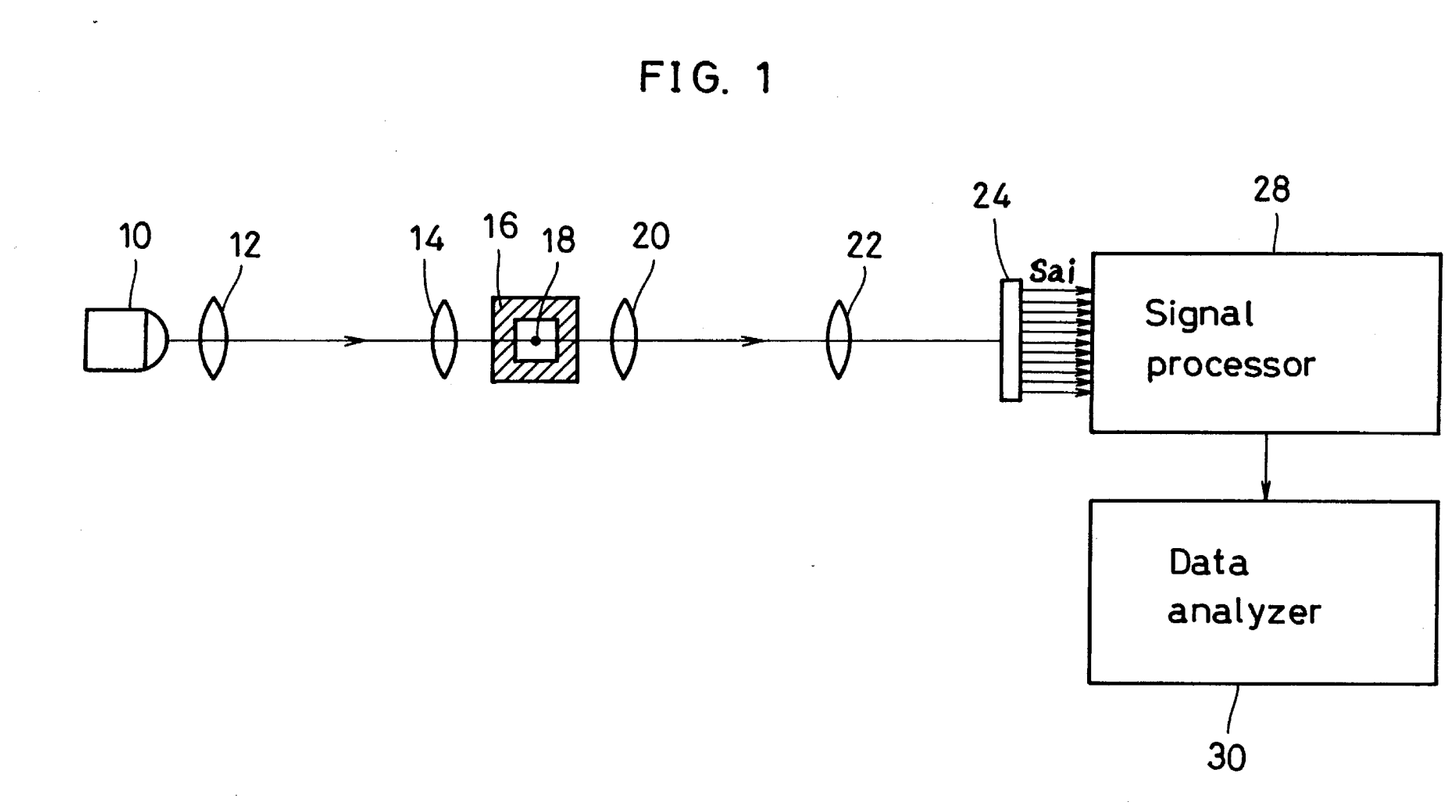
FIG. 1 is a schematic diagram showing an example of an apparatus for analyzing particles according to the present invention.

The present invention provides, as shown in FIG. 1, an apparatus for analyzing particles by discharging a liquid sample containing particles to be analyzed from a nozzle of a flow cell, passing a sheath liquid around the liquid sample to form a sheath flow, emitting light to the sample liquid flow, detecting the light from the particles, and analyzing the particles on the basis of the detected signals, comprising:

a light source for emitting light to the liquid sample, a photo sensor array, comprising a set of tiny photo sensors Pi, in which the photo sensors Pi are arranged in a row in a direction vertical to the moving direction of the particles, particle transmitted light images are focused, and detection signals Sai from the photo sensors Pi are produced in parallel, and a signal processor for parallel processing the detection signals Sai from the photo sensor array to obtain characteristic parameters of individual particles in real time, and processing and operating the signals as desired on the basis of signal group Si undergoing background correction.

Figure 6:
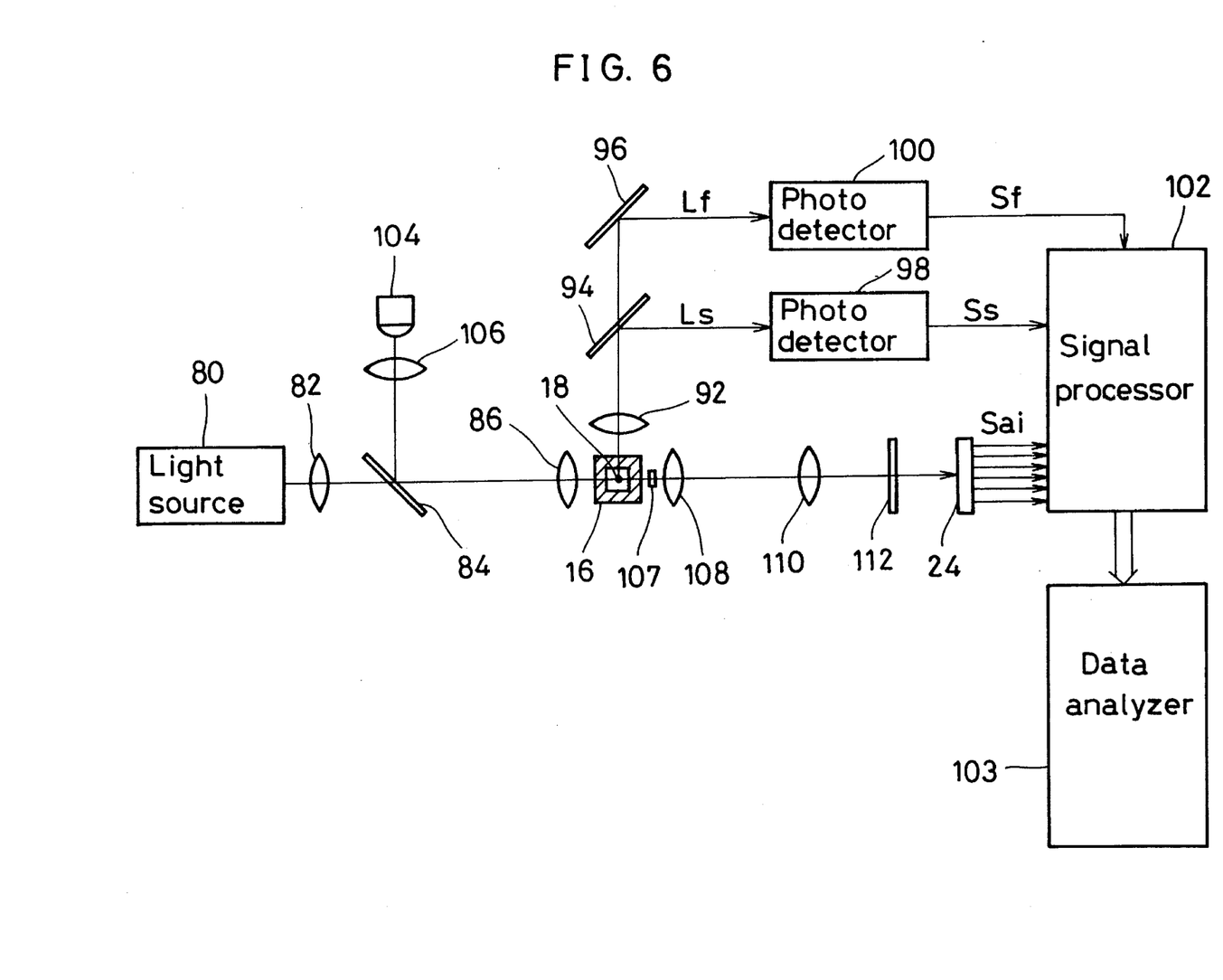
FIG. 6 is a schematic diagram showing another embodiment of an apparatus for analyzing particles according to the present invention.

The present invention also provides, as shown in FIG. 6, an apparatus for analyzing particles by discharging a liquid sample containing particles to be analyzed from a nozzle of a flow cell, passing a sheath liquid around the liquid sample to form a sheath flow, emitting light to the sample liquid flow, detecting the light from the particles, and analyzing the particles on the basis of the detected signals, comprising:

a light source for emitting light to the liquid sample, a photo sensor array, comprising a set of tiny photo sensors Pi, in which the photo sensors Pi are arranged in a row in a direction vertical or perpendicular to the moving direction of particles, particle transmitted light images are focused, and detection signals Sai from the photo sensors Pi are produced in parallel, photo detectors for detecting the light such as scattered light and fluorescent light emitted from the particles, and a signal processor for parallel processing the detection signals Sai from the photo sensor array, and processing signals Ss, Sf from the photo detectors to obtain characteristic parameters of individual particles in real time, and processing and operating the signals as desired on the basis of signal group Si undergoing background correction.

Still further, as shown in FIG. 6, the present invention provides an apparatus for analyzing particles by discharging a liquid sample containing particles to be analyzed from a nozzle of a flow cell, passing a sheath liquid around the liquid sample to form a sheath flow, emitting light to the sample liquid flow, detecting the light from the particles, and analyzing the particles on the basis of the detected signals, comprising:

a first light source for emitting first light to the liquid sample, a photo sensor array, comprising a set of tiny photo sensors Pi, in which the photo sensors Pi are arranged in a row in a direction vertical to the moving direction of particles, particle transmitted light images by the first light are focused, and detection signals Sai from the photo sensors Pi are produced in parallel, a second light source for emitting a second light to the liquid sample, photo detectors for detecting the light such as scattered light and fluorescent light emitted from the particles by the second light, and a signal processor for parallel processing the detection signals Sai from the photo sensor array, and processing signals Ss, Sf from the photo detectors to obtain characteristic parameters of individual particles in real time, and processing and operating the signals as desired on the basis of signal group Si undergoing background correction.

In these apparatuses, it is preferred to obtain the light absorption quantity data Q of individual particles by comprising means for sampling the background correction signal group Si in a specific period, and summing up the magnitude of all signals concerning sampling signal Si (j); i, j∈C of the same particle C.

Figure 7:
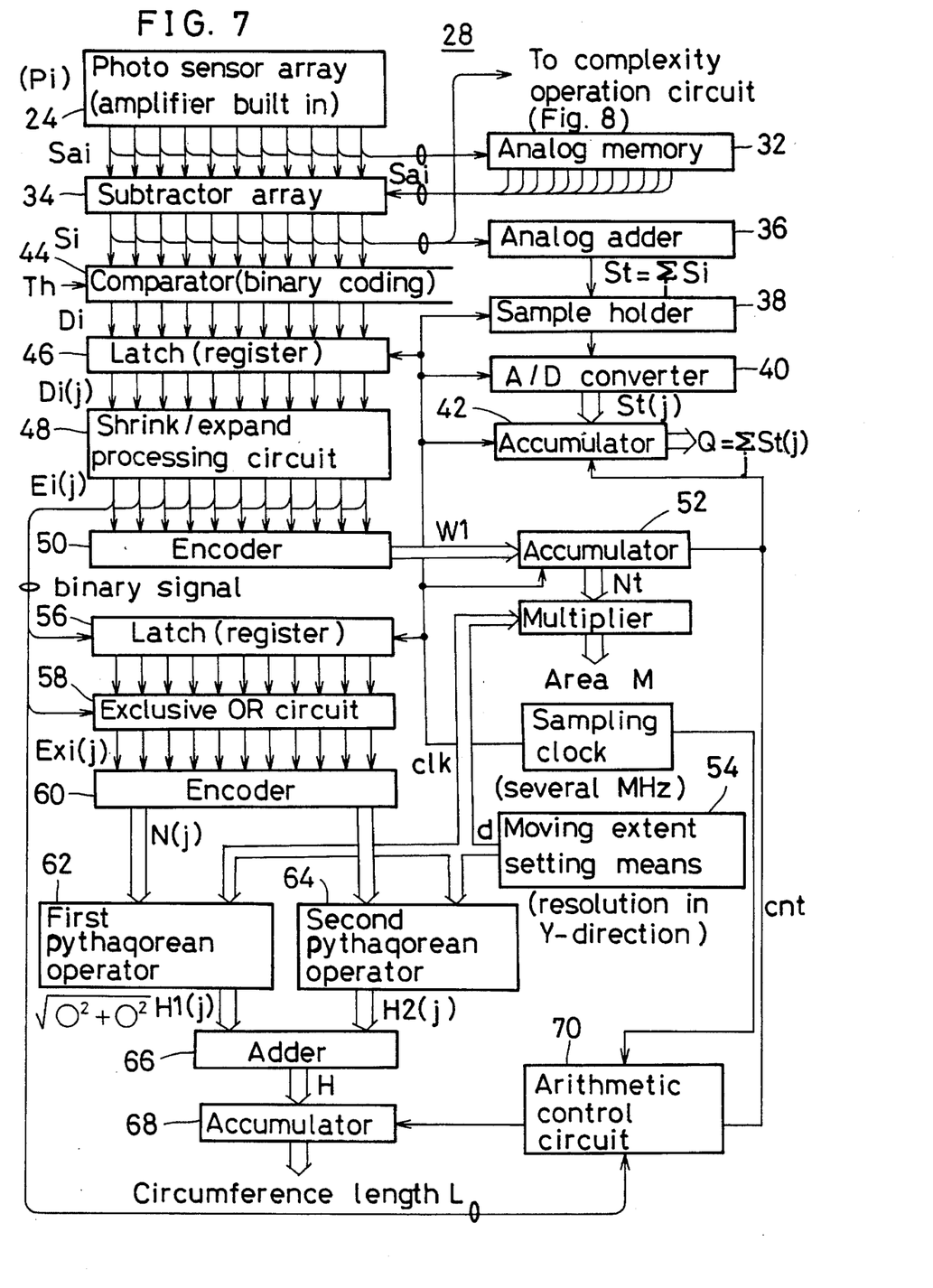
FIG. 7 is a schematic diagram showing an example of an arithmetic circuit for a light absorption quantity, area, circumference length, etc. as a practical example of a signal processing device.

It is also preferred to obtain the particle area data M by, as shown in FIG. 7 comparing means for obtaining binary signal group Di for detecting particle portions by comparing the background correction signal group Si with a specific threshold Th, shrink/expand processing means for sampling the binary signal group Di in a specific period and obtaining binary signal group Ei (j) by shrinking and expanding binary signal group Di; i, j∈C of a same particle in every sampling j, and means for determining the total number Nt of signals indicating particle portions about the binary signal group Ei (j); i, j∈C of a same particle C, and multiplying the signal total number Nt and moving extent data d of particle in one sampling period.

In this case it is preferred to obtain the particle area M1 and nucleus area M2 by using threshold Th1 for detecting entire particles and threshold Th2 for detecting the nucleus.

In the apparatus shown in FIG. 1 or FIG. 6, it is desired to obtain the particle circumference length data L for individual particles by summing up all addition data H of a same particle, as shown in FIG. 7 comparing means for obtaining binary signal group Di for detecting particle portions by comparing the background correction signal group Si with a specific threshold Th, shrink/expand processing means for sampling the binary signal group Di in a specific period and obtaining binary signal group Ei (j) by shrinking and expanding in every sampling j in binary signal group Di(j); i, j∈C of a same particle C, exclusive OR processing means for obtaining binary signal group Exi (j) by calculating an exclusive OR of binary signal group Ei(j) of sampling j and binary signal group Ei (j−1) of sampling j−1, encoder means for obtaining continuous numbers N1 (j), N2 (j) of signals, about binary signal group Eix (j); i, j∈C of a same particle C, arithmetic means for calculating the square root data Hi (j), H2 (j) of square sum of the signal numbers N1 (j), N2 (j) and moving extent data d of particle in one sampling period, and addition means for summing the square root data Hi (j), H2 (j).

Moreover, in the apparatus shown in FIG. 1 or FIG. 6, it is desired to obtain the complexity data F of individual particles by comprising means for sampling the difference ΔSi of adjacent signals Si, Si−1 of the background correction signal group Si, and summing up the magnitude of all signals about the sampling signal ΔSi (j); i, j∈C of a same particle C.

The characteristic parameters include, for example, light absorption (extinction) information of the particle and morphological information of the particle. The light absorption information of the particle are defined by, for example, the light absorption quantity Q of the particle, or light absorption quantity Q and absorbance R of the particle.

The absorbance R is obtained by dividing the light absorption quantity Q by the particle area S, and the morphological information is selected from a group consisting of particle area SC, particle circumference length L, particle width W, complex quantity in particle F, and nucleus area SN, or the morphological information may be also selected from a group consisting of particle area M1, particle circumference length L, particle width W, complex quantity in particle F, nucleus area M2, particle roundness B, particle complexity G, and nucleus area ratio NC.

The particle complexity C is obtained by dividing the particle complex quantity F by the particle area S, the particle roundness B is obtained by dividing the particle area S by the square $L^2$ of the particle circumference length L, and the nucleus area ratio NC is obtained by dividing the nucleus area M2 by the particle area M1.

DETAILED DESCRIPTION OF THE PREFERRED EMBODIMENTS

Referring now to the drawings, some of the preferred embodiments of the present invention are described in detail below.

FIG. 1 shows an embodiment of an apparatus for analyzing particles of the present invention, illustrating the basic construction for sensing particles moving in a fluid by a photo sensor array.

The sample containing particles to be analyzed is discharged from a nozzle (not shown) of a flow cell 16 composed of a transparent material such as glass or plastic, and it is surrounded with a sheath liquid to form a sample fine flow. The light emitted from a light source 10 is formed into parallel light by a collimator lens 12, is reduced by a condenser lens 14, and is illuminated in a slender form to be matched with a photo sensor array detection area A1 as shown in FIG. 2.

Figure 2:
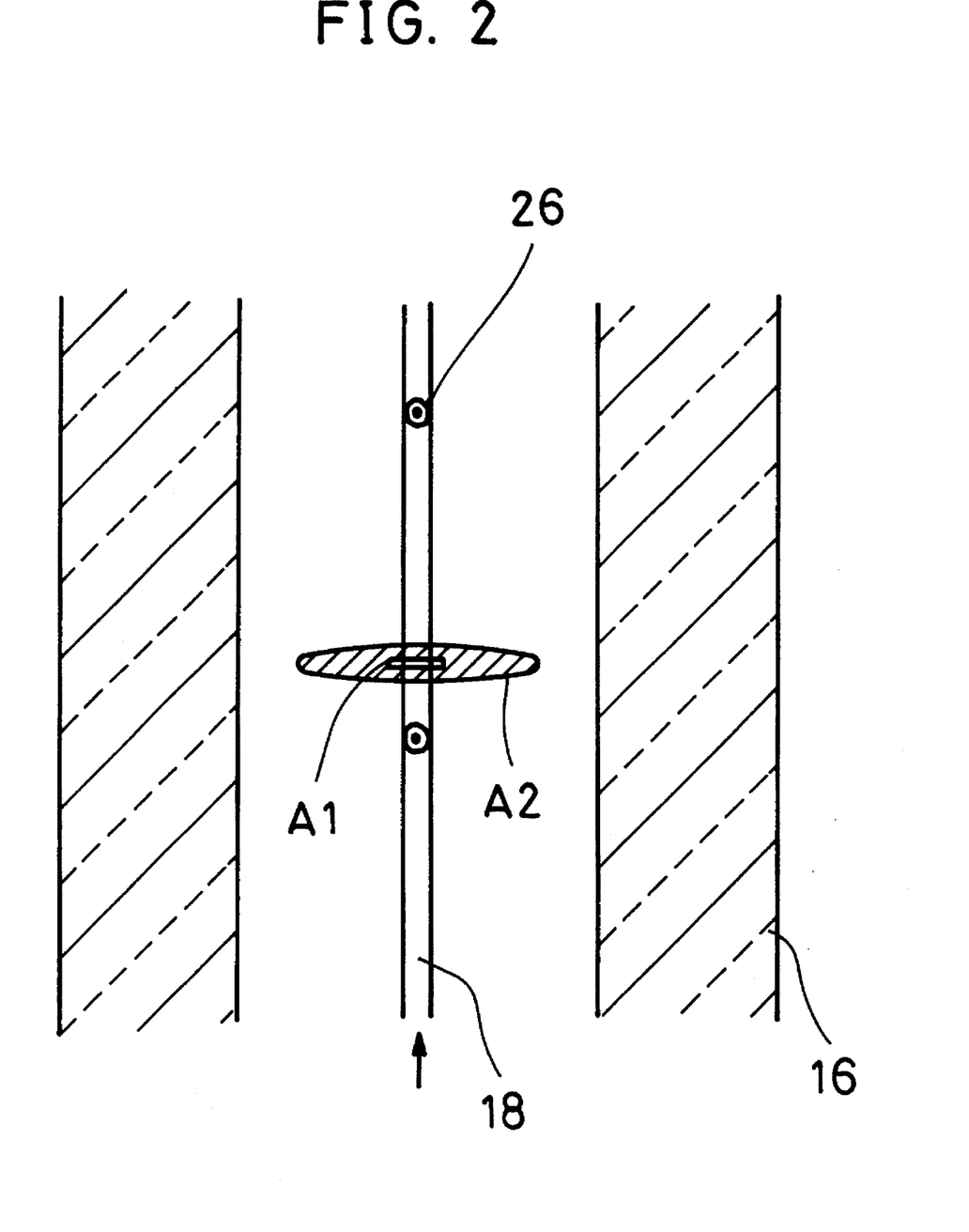
FIG. 2 is a partially magnified sectional view showing the state of observing the flow cell from the optical axis side in FIG. 1.

FIG. 2 is partially magnified view observing the flow cell 16 from the optical axis side. Symbol A2 denotes the light illumination region from the light source. Numeral 26 represents a particle, for example, a cell, and the oblong detection area A1 is so set as to cross a sample flow 18 of, for example, 10 to 20 µm in width. The light from the detection area A1 is focused on the reception plane of a photo sensor array 24 by means of objective lens 20 and projection lens 22.

Figure 3A:
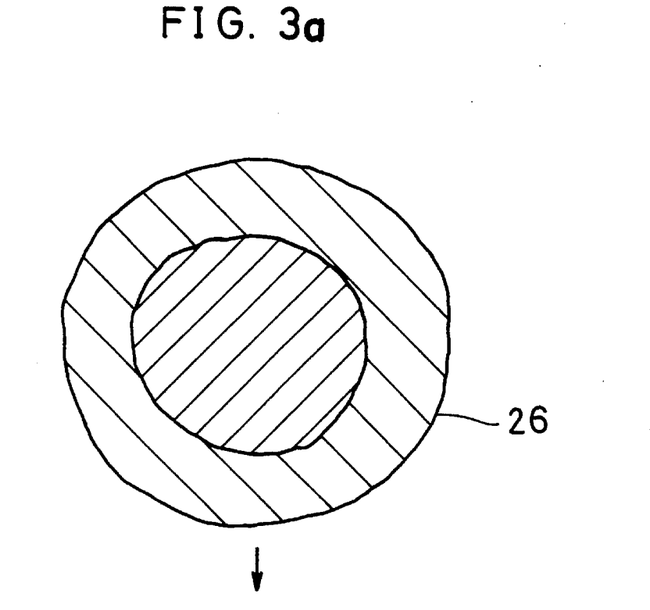
FIG. 3 is an explanatory diagram showing an example of detection signal by the photo sensor array in FIG. 1.
Figure 3B:
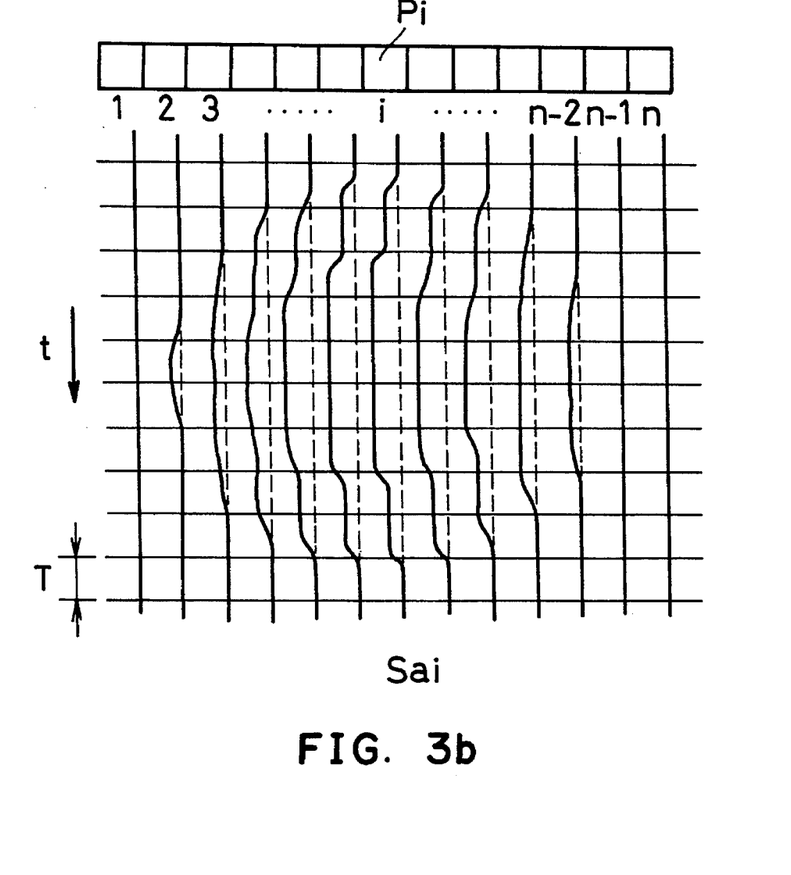

The photo sensor array 24 is constructed, as shown in FIG. 3, of tiny photo sensors Pi; i=1, 2, ..., n arranged in a row. As the detection signals from the photo sensor array 24, signals Sai depending on the quantity of light received by the photo sensors Pi; i=1, 2, ..., n are delivered in parallel. In FIG. 3, the time axis t is plotted downward from the top, and when the particle 26 passes the detection area A1, the detection signals Sai of the photo sensors Pi vary with the passing of time t. That is, as the particle 26 crosses the detection area A1, exposure to each photo sensor Pi is cut off, and the detection signals Sai are changed to the minus side. In FIG. 3, the changing range is i=2 to n–2. While the particle 26 is not passing the detection area A1, or in the detection signals of photo sensors corresponding to the positions not shielded by the passing particle (in FIG. 3, i=1, n=1, n), the level remains high and unchanged.

These detection signals Si of parallel outputs are processed parallel in a signal processing device 28 shown in FIG. 1, and the morphological information and light absorption (extinction) quantity of the particle are obtained in real time. Various data thus obtained are processed in a data analyzing device 30, and developed into scattergram or histogram, and the particles are classified and analyzed.

Processing of detection signals Sai from the photo sensor array 24 is explained below. While the particle 26 is not crossing the detection area A1 of the photo sensor array 24, the level of detection signals Sai from the photo sensors Pi is not always the same. It is estimated to be due to fluctuations of sensitivity of the photo sensors Pi, and nonuniformity of the light illumination intensity of the detection area A1 in the longitudinal direction.

Therefore, in order to capture changes in the detection signals Sai from the photo sensors Pi at high precision, the level Si0 of the detection signal of the photo sensors Pi while a particle is not passing, is held, and the difference from this signal level Si0 is captured as a signal change. That is, the detection signals from the photo sensor array 24 are processed by background correction.

Figure 4:
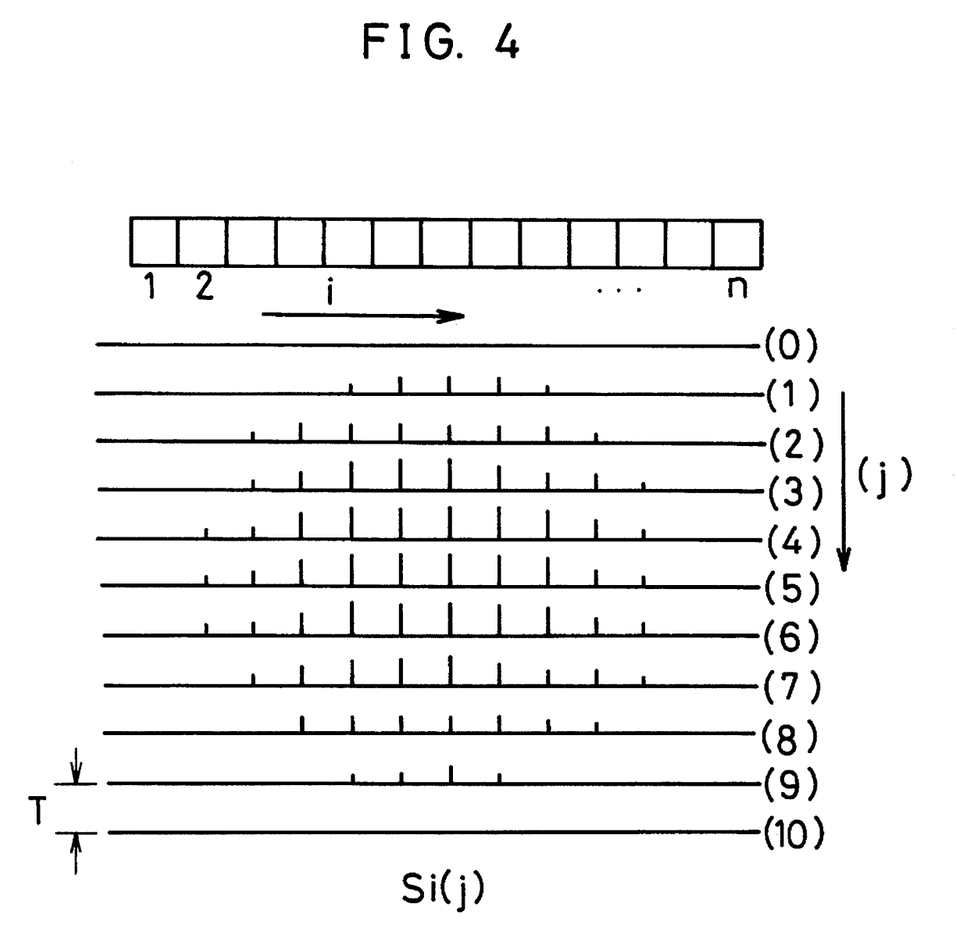
FIG. 4 is an explanatory diagram showing an example of a sampling signal after background correction.

Next, as shown in FIG. 4, the detection signals Si from the photo sensor array after background correction are sampled in every period T (several hundreds of nanoseconds). Symbol j denotes the sampling cycle number.

Figure 5:
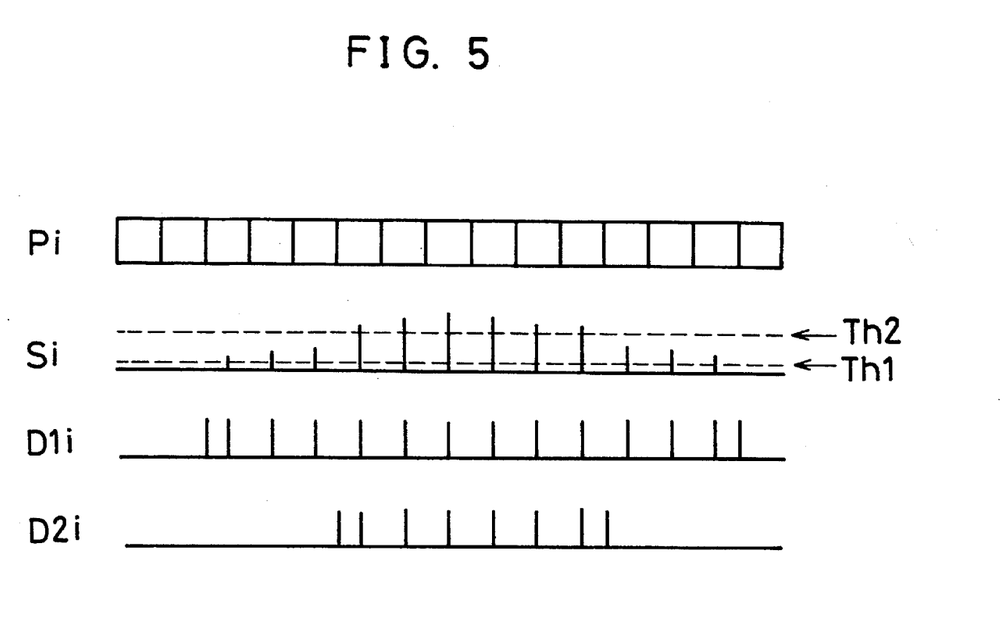
FIG. 5 is an explanatory diagram showing a binary coded example of a sampling signal.

The signal Si (j) thus corrected for background and sampled is compared with the threshold level Th1 for extracting the entire particle by the comparator, and the threshold level Th2 for extracting the portion of the nucleus, and is coded in binary signal in every sampling. Its example is shown in FIG. 5.

An example of the signal processing device 28 for obtaining the area, circumference length, light absorption quantity, and complexity of each particle actually passing the detection unit is explained below by reference to FIG. 7. The photo sensor array 24 is constructed of hybrid type IC, tiny PIN photo diodes Pi being arranged in one lateral row at pitches of scores of micron meters, and adding a preamplifier to each photo diode Pi. In the first place, while the particle is not passing the detection area of the photo sensor array, the detection signal Si0 of each photo sensor is held in an analog memory 32. The difference Si=Si0–Sai between this signal level Si0 and the detection signal Sai obtained when the particle passes the detection area is calculated in a subtractor array 34. The detection signals Si of the photo sensors thus undergo background correction a are all summed up in an analog adder 36, and the sum total signal St (see formula (1)) is sample-held in every sampling cycle (hundreds of nanoseconds), and A/D converted.

$$St = \sum_i Si \quad (1)$$

The data St (j) is summed up in the number of times of sampling by an accumulator 42 while the particle passes through the photo sensor array, and the light absorption quantity Q corresponding to the particle is determined in real time. The number of times a particle is sampled is determined by the moving speed, size, and sampling frequency of the particle.

For example, supposing the particle moving speed to be 3 m/sec, its size to be 12 μm, and its sampling cycle to be 300 nsec, the number of sampling times of that particle is $12/3=10^6 \times 300 \times 10^{-9} \times 13.3$ that is, 13 times. The greater the number of sampling times, the higher becomes the precision of the obtained characteristic parameter data such as the area, circumference length, light absorption quantity, and complexity.

The operation (arithmetic) processing for calculating the area and circumference length of a particle is described below. The signal Si corrected for background by the subtractor array 34 is compared with the threshold level Th1 to extract the entire particle by a comparator 44, and is coded into a binary signal. Symbol Di refers to a binary signal. The binary signals change from moment to moment by the passage of sampled particles (latched) every several hundred nanoseconds by a latch 46, and sent to a shrink/expand processing circuit 48 as signals Di (j). The shrink/expand processing circuit 48 processes shrinking to eliminate impurity and noise signals, and processes expanding for filling up with binary signals corresponding to the abnormal bright portions in the particles due to lens effect or the like of the particle itself. The signals at this time are Ei (j). Shrinking is the process of setting the binary signal corresponding to the sensor of interest to low (0) if either one of the binary signals of the adjacent sensors of the photo sensor of interest is low (0). Expanding is the process of setting the binary signal corresponding to the sensor of interest high (1) if either one of the binary signals corresponding to the adjacent sensors to the photo sensor of interest is high (1). By repeating such processing several times, large holes in the particles (the portions brighter than the background) will be filled up. By this expanding processing, however, since the binary signals become more than the number corresponding to the size of the actual particles, shrinking processes are conducted later at the same number as that of the expanding processes.

The number of binary signals thus obtained is coded into a binary number by an encoder 50. This binary data W1 is summed up by an accumulator 52 by the number of times of sampling while the particle passes through the photo sensor array, and the value obtained is multiplied by the moving distance d of the particle in the sampling cycle period, and the area M corresponding to the particle is calculated in real time. Numeral 54 refer to the moving extent setting means for setting the particle moving distance d.

Figure 9:
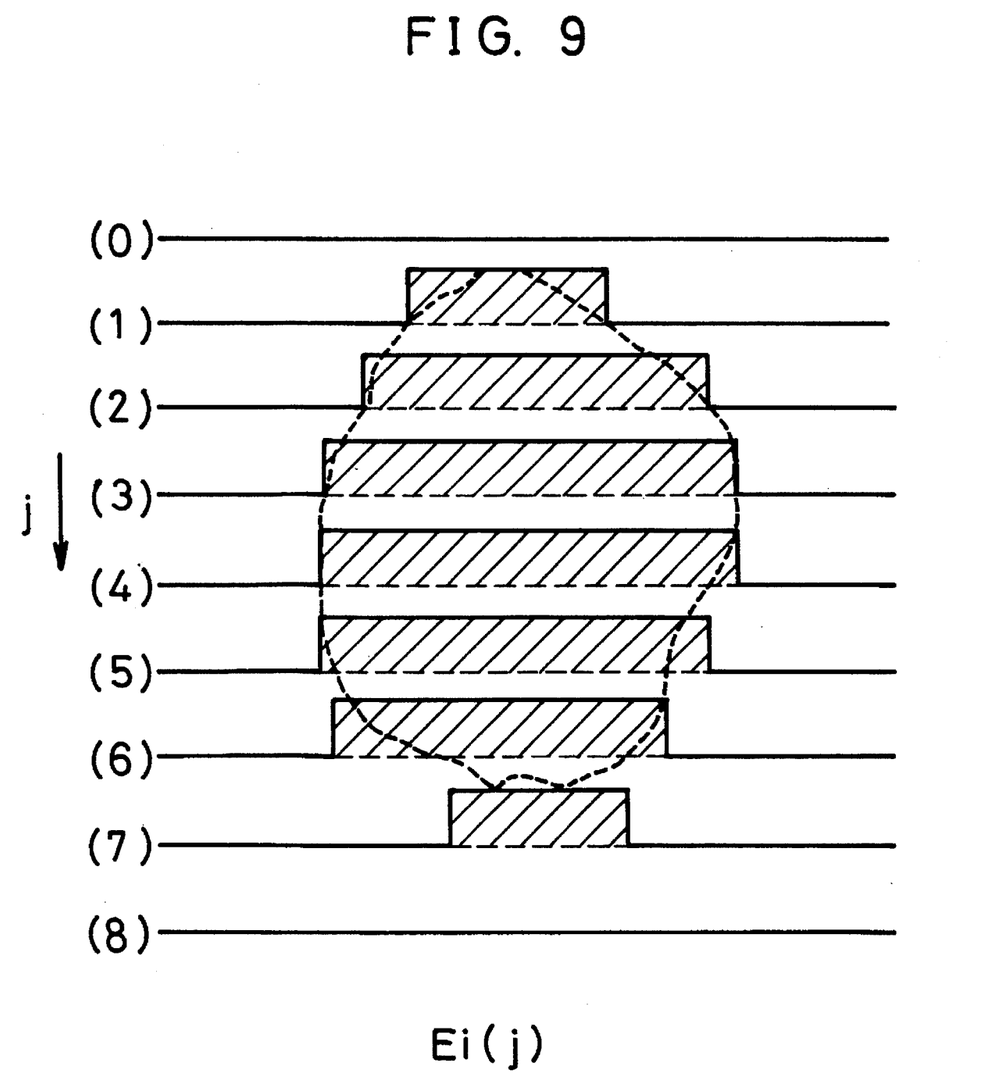
FIG. 9 is an explanatory diagram showing an example of a logic signal after binary coding processing.

On the other hand, the binary signals Ei (j) thus processed by shrinking and expanding in the processing circuit 48 are successively held in a latch register 56 by a sampling clock, and the exclusive OR signal Exi (j) of the binary signal Ei (j–1) of one sampling cycle before j–1 a the one held in the register, and the binary signal Ei (j) of the present cycle j is calculated by an exclusive OR circuit 58. This mode is shown in FIG. 9 and FIG. 10.

Figure 10:
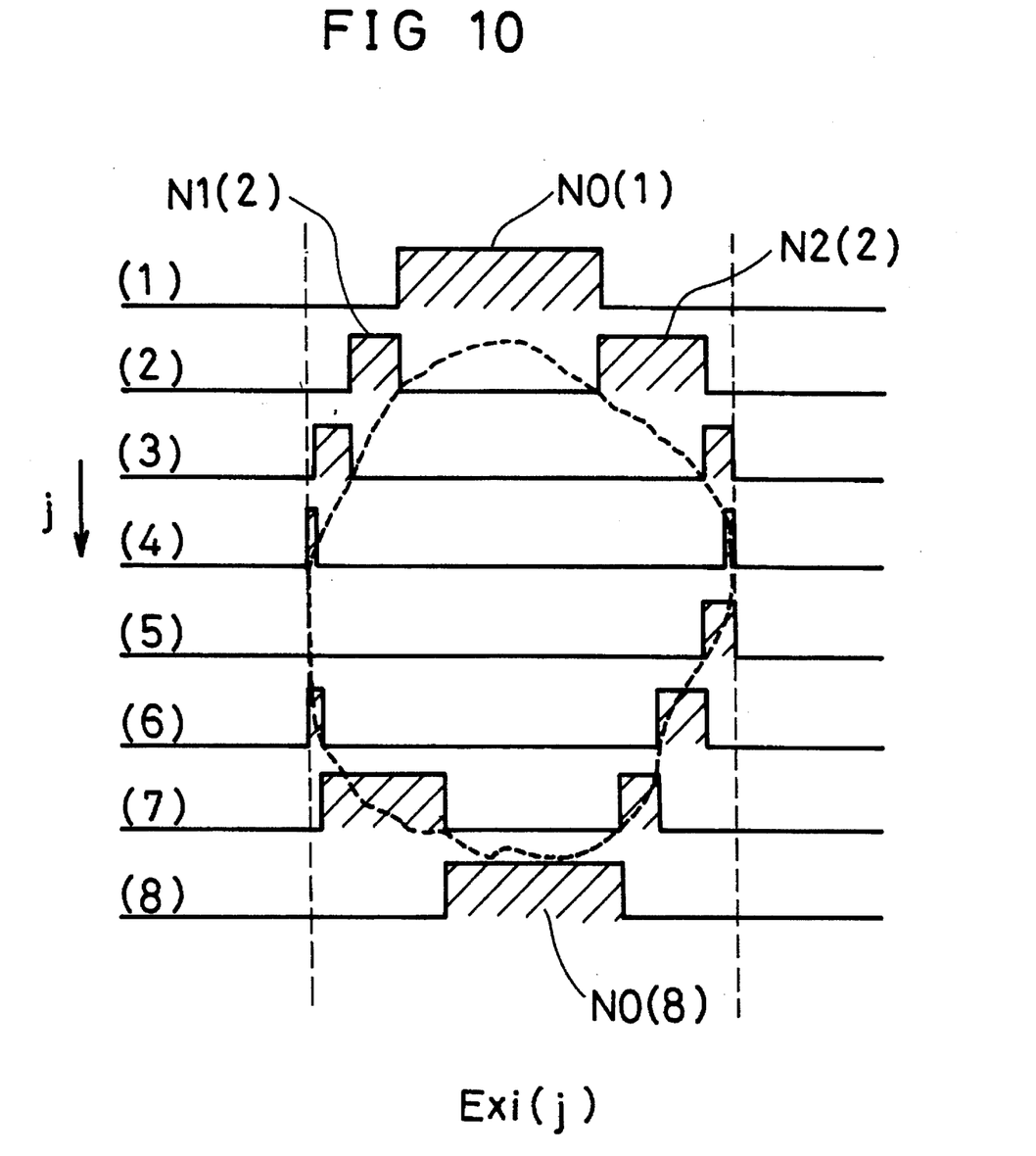
FIG. 10 is an explanatory diagram showing an example of an exclusive OR signal.

The exclusive OR signal Exi (j) indicated by oblique lines in FIG. 10 is determined by an encoder 60 (see FIG. 7) in every sampling cycle of several hundred nsec. In the case of a cycle having two cycles of exclusive OR signals, the square root of the sum of the square of the number of signals at the left side and the square of the distance L of the particle moving in the sampling cycle period is calculated by a first Pythagorean operator 62. Similarly, the right side signals are calculated by a second Pythagorean operator 64. Both square roots are summed up by an adder 66. Further, the total values are summed up by an accumulator 68 for every particle, and the approximate value L of the circumferential length of the particle is calculated in real time.

By squaring the thus obtained circumference length L and dividing the surface area S by this value $L^2$, the roundness of the particle is obtained in real time.

An operation (arithmetic) control circuit 70 shown in FIG. 7 determines the range of the sampling cycle j for individual particles, and creates a control signal Cnt for controlling the operation of the individual accumulators in the period. That is, the value of each accumulator is returned to zero before the start of a sampling cycle on each particle, and in every sampling period j corresponding to the particle, the values to be entered in each accumulator are summed up, and upon completion of sampling of the specific particle, the parameters such as area, light absorption quantity and circumference length are obtained.

Figure 8:
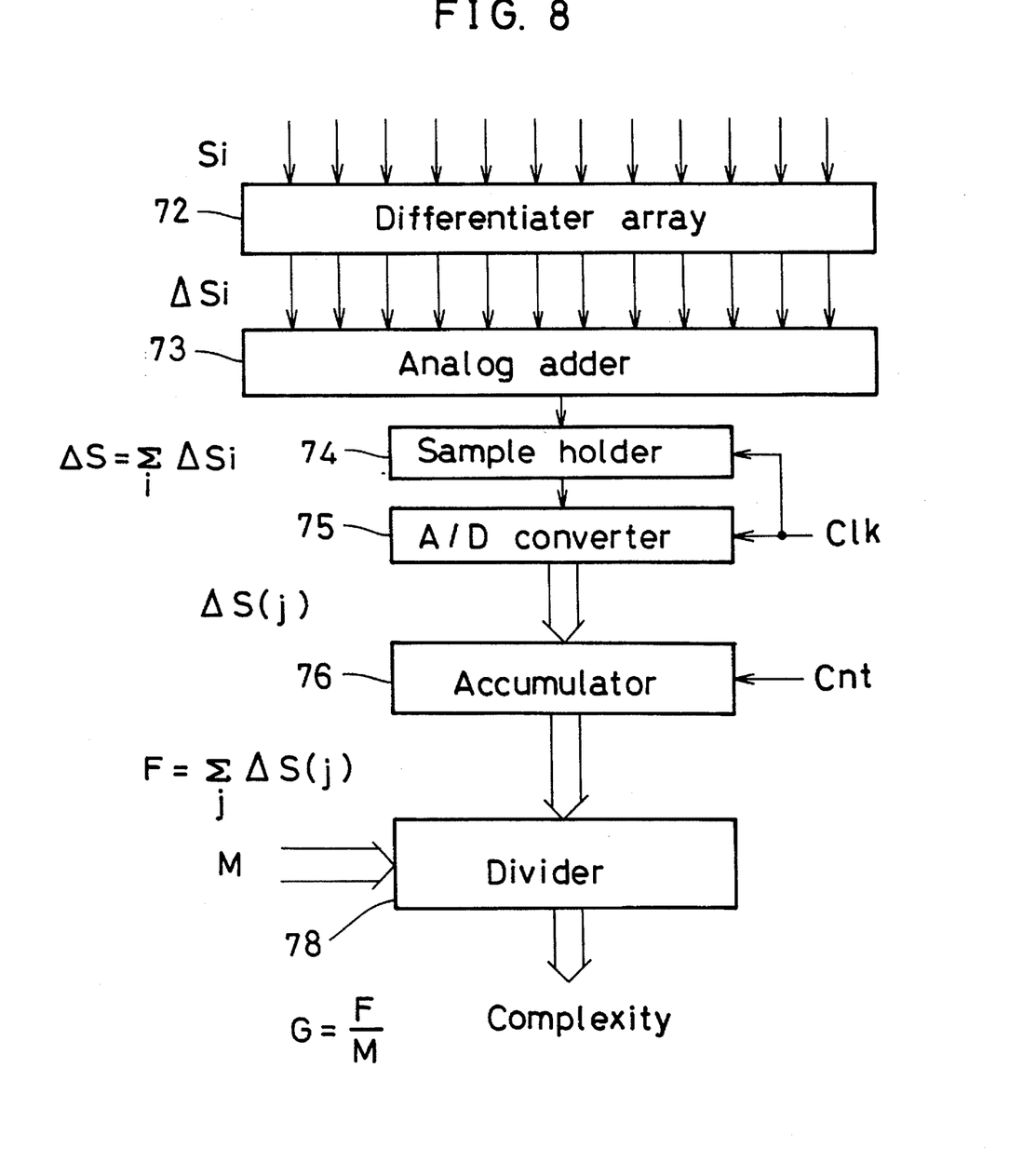
FIG. 8 is a schematic diagram showing an example of a complexity operating (arithmetic) circuit.

To determine the complexity F, the signal (background correction signal) Si from the subtractor array 34 in FIG. 7 is compared with the signal level corresponding to the adjacent photo sensors by a differential array 72 shown in FIG. 8, and the difference ΔSi is obtained. The differential signals ΔSi are all summed up in an analog adder 73, and the signal ΔS is sample-held in a sampling holder 74 in every sampling cycle j, and is A/D converted by an A/D converter 75. The values ΔS (j) are summed up by an accumulator 76 over the sample cycle corresponding to one particle, and the complexity F of the particle is obtained. Further, by dividing this value by the area M, the complexity G is obtained.

When analyzing a cell having a nucleus inside, as the threshold level to the comparator 44 shown in FIG. 7, the threshold level Th1 for extracting the entire cell and the threshold level Th2 for extracting only the portion of the nucleus are set, and the above-mentioned parameters may be obtained individually. By dividing the area SN of the nucleus portion by the area SC of the entire cell, the area ratio of nucleus (N/C ratio) NC may be determined.

In this way, in individual particles flowing at high speed in the flow cell, the morphological parameters such as area, circumference length, roundness, light absorption quantity and complexity are obtained in real time.

Another embodiment of an apparatus for analyzing particles by adding the detecting system and signal processing system by the photo array sensor mentioned above to the conventional flow cytometer is shown in FIG. 6.

In FIG. 6, a first light source 80 is a laser light source used in the conventional flow cytometer, and, for example, an argon gas laser is used. This laser light is reduced to a slender form as shown in FIG. 2 by a cylindrical lens 82 and a condenser lens 86 through a first dichroic mirror 84, and is emitted to a sample flow 18 in a flow cell 16. A side scatter light Ls obtained when a particle in the sample flow 18 passes a laser illumination region is collected by an objective lens 92, and is reflected by a second dichroic mirror 94, then received by a photo detector 98, for example, a photo multiplier. On the other hand, a side fluorescent light Lf is collected by an objective lens 92, transmits through a second dichroic mirror 94, and is reflected by a third dichroic mirror 96, then received by a photo detector 100. Detection signals Ss, Sf received and multiplied by respective photo detectors (photo multiplies) 98, 100 are sent to a signal processing device 102, and the individual light intensities are obtained in real time.

A second light source 104 is an exclusive light source for obtaining the morphological information and light absorption quantity of the particle. For this purpose, and a light source of low coherency is desired. For example, a superluminescence diode (SLD) emitting near infrared light is used. Since this light source 104 has much lower coherency than the semiconductor diode, a transmitted light image of less obvious interference fringe is focused on the photo sensor array, and information (parameters) of higher precision are obtained. Where the interference fringe does not matter much or lower cost is desired, the light source 104 may be replaced by the light source 80. Or, the laser beam of the light source 80 may be emitted while lowering the coherency through an optical fiber. (Not shown)

The light of the light source 104 is reflected by the first dichroic mirror 84, and is finely reduced by the collimator lens 106 and condenser lens 86, and emitted to the sample flow 18. The light passing (transmitting) the sample flow 18 is focused on the photo sensor array 24 by a projector lens 110 through an objective lens 108. A beam stopper 107 cuts direct light from the light source 80, and a filter 112 cuts transmitted light at the wavelength by the light source 80.

The transmitted light received by the photo sensor array 24 is converted into an electric signal corresponding to the light intensity to each photo sensor Pi, and these detection signals Si are sent in parallel to the signal processing device 102. Herein, for the individual particles passing through the flow cell 16, the parameters such as area, circumference length, roundness, light absorption quantity and complexity are obtained in real time.

Various parameters obtained in this way are sent into a data analyzing device 103, and are developed into scattergrams or histograms by the combination of various parameters, and are further subjected to statistical processing and multi-variable analysis processing, and the particles are classified and abnormal particles judged. Being thus constructed, the present invention brings about the following effects.

(1) Without using an expensive video camera or image processing device, it is constructed to process in parallel the detection signal groups delivered parallel from elements by using a photo sensor array having tiny photo detection elements (photo sensors) arranged in a row, and hence the morphological information and light absorption quantity of individual moving particles may be obtained in real time.

(2) By combining the conventional flow cytometer or cell sorter with the apparatus for analyzing particles comprising the detecting system and signal processing system of the present invention, novel parameters such as the morphological information and light absorption quantity may be obtained aside from the optical features of the individual particles (scattered light intensity, fluorescent intensity, etc., so that the particles may be analyzed at high precision.

(3) By parallel processing of detection signals from a tiny photo sensor array, the above-mentioned parameters are obtained, and therefore the sampling cycle of detection signals per line can be notably shortened, and the flow velocity of the sample flow can be accelerated to several meters/second, that is, nearly equal to the level to the flow velocity in the conventional flow cytometer, so that the number of particles to be analyzed per unit time may be sufficiently maintained.

(4) The sample flow is not a broad (wide) flat flow, but is a flow of round or square section, and it is very rare that two or more particles pass simultaneously the detection area side by side, so that only one set of operator (arithmetic means) may be enough for calculating the above-mentioned parameters, while complicated signal processing for dividing regions for adjacent particles may not be required.

(5) As the light source for projecting to the photo sensor array, when using the superluminescence diode of small coherency, the particle transmitted light images almost free of interference fringe may be projected on the photo sensor array.

(6) The detection position by the laser light in the conventional flow cytometer and the detection position by the photo sensor array may be matched, the optical system may be designed in a compact form, and the conventional fluorescence and scattered light data of individual particles may be easily combined with the data of morphological information and light absorption quantity.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the invention as defined in the appended claims.

What is claimed is:

1. An apparatus for analyzing particles by discharging a liquid sample containing particles to be analyzed from a nozzle of a flow cell, passing a sheath liquid around the liquid sample to form a sheath flow, emitting light to the sample liquid flow, detecting the light from the particles, and analyzing the particles on the basis of the detected signals, comprising:

a light source for emitting the light to the liquid sample, a photo sensor array, comprising a set of photo sensors arranged in a row in a direction perpendicular to the moving direction of particles, relative to which particle transmitted light images are focused, said set of photo sensors generating detection signals produced in parallel, and a signal processor for parallel processing the detection signals from the photo sensor array to obtain characteristic parameters, such as morphological information, adsorption information, and the like, of individual particles in real time, and processing and operating on the detection signals as desired on the basis of background correction signals.

2. An apparatus for analyzing particles according to claim 1, further comprising means for sampling the background correction signals of the photo sensor array signals in a specific period, and summing up the magnitude of all signals concerning the same particle.

3. An apparatus for analyzing particles according to claim 1, further comprising:

comparing means for obtaining a binary signal group for detecting particle portions by comparing the background correction signals of the photo sensor array signals with a specific threshold, shrink/expand processing means for sampling the binary signal group in a specific period and obtaining a sampling binary signal group by shrinking and expanding the binary signal group of the same particle in every sampling, and means for determining the total number of signals indicating particle portions about the sampling binary signal group of the same the particle, and multiplying the signal total number and moving extent data of the particle in one sampling period.

4. An apparatus for analyzing particles according to claim 3, wherein the particle area and nucleus area are obtained by using a threshold for detecting the entire particle and a threshold for detecting the nucleus.

5. An apparatus for analyzing particles according to claim 1, wherein particle circumference length data for individual particles are obtained by summing up all addition data of the same particle, further comprising:

comparing means for obtaining a binary signal group for detecting particle portions by comparing the background correction signal group with a specific threshold, shrink/expand processing means for sampling the binary signal group in a specific period and obtaining a binary signal group by shrinking and expanding in every sampling in the binary signal group of the same particle, exclusive OR processing means for obtaining a binary signal group by calculating an exclusive OR of the binary signal group of the sampling and binary signal group of one preceding sampling, encoder means for obtaining continuous numbers of signals, exclusive OR binary signal group of the same particle, arithmetic means for calculating the square root data of the square sum of the signal numbers and moving extent data of the particles in one sampling period, and addition means for summing the square root data.

6. An apparatus for analyzing particles according to claim 1, further comprising means for obtaining the complexity data of individual particles by sampling the difference of adjacent signals of the background correction signal group, and summing up the magnitude of all the sampling difference signals of the same particle.

7. An apparatus for analyzing particles according to claim 1, wherein the characteristic parameters comprise light absorption information of the particle.

8. An apparatus for analyzing particles according to claim 1, wherein the characteristic parameters comprise morphological information of the particle.

9. An apparatus for analyzing particles according to claim 7, wherein one of the light absorption information comprises the light absorption quantity of the particle.

10. An apparatus for analyzing particles according to claim 7, wherein the light absorption information comprises the light absorption quantity and absorbance of the particle.

11. An apparatus for analyzing particles according to claim 10, wherein the absorbance is obtained by dividing the light absorption quantity by the particle area.

12. An apparatus for analyzing particles according to claim 8, wherein at least one of the morphological information is/are selected from a group consisting of particle area, particle circumference length, particle width, and complex quantity in the particle, and nucleus area.

13. An apparatus for analyzing particles according to claim 8, wherein at least one of the morphological information is/are selected from a group consisting of particle area, the particle circumference length, particle width, and complex quantity in the particle, nucleus area, particle roundness, particle complexity, and nucleus area ratio.

14. An apparatus for analyzing particles according to claim 13, wherein particle complexity is obtained by dividing the particle complex quantity by the particle area.

15. An apparatus for analyzing particles according to claim 13, wherein the particle roundness is obtained by dividing the particle area by the square of the particle circumference length.

16. An apparatus for analyzing particles according to claim 13, wherein the nucleus area ratio is obtained by dividing the nucleus area by the particle area.

17. An apparatus for analyzing particles by discharging a liquid sample containing particles to be analyzed from a nozzle of a flow cell, passing a sheath liquid around the liquid sample to form a sheath flow, emitting light to the sample liquid flow, detecting the light from the particles, and analyzing the particles on the basis of the detected signals, comprising:

a light source for emitting the light to the liquid sample, a photo sensor array, comprising a set of photo sensors arranged in a row in a direction perpendicular to the moving direction of particles, relative to which particle transmitted light images are focused, said set of photo sensors generating detection signals produced in parallel, photo detectors for detecting light, such as scattered light and/or fluorescent light, emitted from the particles, and a signal processor for parallel processing the detection signals from the photo sensor array, and processing signals from the photo detectors to obtain characteristic parameters, such as morphological information, adsorption information, and the like, of individual particles in real time, and processing and operating on the signals as desired on the basis of background correction signals.

18. An apparatus for analyzing particles according to claim 17, further comprising means for sampling the background correction signals of the photo sensor array signals in a specific period, and summing up the magnitude of all signals concerning the same particle.

19. An apparatus for analyzing particles according to claim 17, further comprising:

comparing means for obtaining a binary signal group for detecting particle portions by comparing the background correction signals of the photo sensor array signals with a specific threshold, shrink/expand processing means for sampling the binary signal group in a specific period and obtaining a sampling binary signal group by shrinking and expanding the binary signal group of a same particle in every sampling, and means for determining the total number of signals indicating particle portions about the sampling binary signal group of the same the particle, and multiplying the signal total number and moving extent data of the particle in one sampling period.

20. An apparatus for analyzing particles according to claim 19, wherein the particle area and nucleus area are obtained by using a threshold for detecting the entire the particle and a threshold for detecting the nucleus.

21. An apparatus for analyzing particles according to claim 17, wherein particle circumference length data for individual particles are obtained by summing up all addition data of the same particle, further comprising:

comparing means for obtaining a binary signal group for detecting particle portions by comparing the background correction signal group with a specific threshold, shrink/expand processing means for sampling the binary signal group in a specific period and obtaining a binary signal group by shrinking ad expanding in every sampling in the binary signal group of the same particle, exclusive OR processing means for obtaining a binary signal group by calculating an exclusive OR of the binary signal group of the sampling and binary signal group of one preceding sampling, encoder means for obtaining continuous numbers of signals, exclusive OR binary signal group of the same particle, arithmetic means for calculating the square root data of the square sum of the signal numbers and moving extent data of the particles in one sampling period, and addition means for summing the square root data.

22. An apparatus for analyzing particles according to claim 17, further comprising means for obtaining the complexity data of individual particles by sampling the difference of adjacent signals of the background correction signal group, and summing up the magnitude of all signals about the sampling difference signals of the same particle.

23. An apparatus for analyzing particles according to claim 17, wherein the characteristic parameters comprise light absorption information of the particle.

24. An apparatus for analyzing particles according to claim 17, wherein the characteristic parameters comprise morphological information of the particle.

25. An apparatus for analyzing particles according to claim 23, wherein one of the light absorption information comprises the light absorption quantity of the the particle.

26. An apparatus for analyzing particles according to claim 23, wherein the light absorption information comprises the light absorption quantity and absorbance of the particle.

27. An apparatus for analyzing particles according to claim 26, wherein the absorbance is obtained by dividing the light absorption quantity by the particle area.

28. An apparatus for analyzing particles according to claim 24, wherein at least one of the morphological information is/are selected from a group consisting of particle area, the particle circumference length, the particle width, and complex quantity in the particle, and nucleus area.

29. An apparatus for analyzing particles according to claim 24, wherein at least one of the morphological information is/are selected from a group consisting of particle area, particle circumference length, particle width, and complex quantity in the particle, nucleus area, particle roundness, particle complexity, and nucleus area ratio.

30. An apparatus for analyzing particles according to claim 29, wherein the particle complexity is obtained by dividing the particle complex quantity by the particle area.

31. An apparatus for analyzing particles according to claim 29, wherein the particle roundness is obtained by dividing the particle area by the square of the particle circumference length.

32. An apparatus for analyzing particles according to claim 29, wherein the nucleus area ratio is obtained by dividing the nucleus area by the particle area.

33. An apparatus for analyzing particles by discharging a liquid sample containing particles to be analyzed from a nozzle of a flow cell, passing a sheath liquid around the liquid sample to form a sheath flow, emitting light to the sample liquid flow, detecting the light from the particles, and analyzing the particles on the basis of the detected signals, comprising:

a first light source for emitting a first light to the liquid sample, a photo sensor array, comprising a set of photo sensors arranged in a row in a direction perpendicular to the moving direction of particles, relative to which particle transmitted light images by the first light are focused, said set of photo sensors generating detection signals produced in parallel, a second light source for emitting a second light to the liquid sample, photo detectors for detecting the light such as scattered light and/or fluorescent light emitted from the particles by the second light, and a signal processor for parallel processing the detection signals from the photo sensor array, and processing signals from the photo detectors to obtain characteristic parameters, such as morphological information, adsorption information, and the like, of individual particles in real time, and processing and operating on the signals as desired on the basis of background correction signals.

34. An apparatus for analyzing particles according to claim 33, further comprising means for sampling the background correction signals of the photo sensor array signals in a specific period, and summing up the magnitude of all signals concerning the same particle.

35. An apparatus for analyzing particles according to claim 33, further comprising:

comparing means for obtaining a binary signal group for detecting particle portions by comparing the background correction signals of the photo sensor array signals with a specific threshold, shrink/expand processing means for sampling the binary signal group in a specific period and obtaining a sampling binary signal group by shrinking and expanding the binary signal group of a same particle in every sampling, and means for determining the total number of signals indicating particle portions about the sampling binary signal group of the same particle, and multiplying the signal total number and moving extent data of the particle in one sampling period.

36. An apparatus for analyzing particles according to claim 35, wherein the particle area and nucleus area are obtained by using a threshold for detecting the entire particle and a threshold for detecting the nucleus.

37. An apparatus for analyzing particles according to claim 33, wherein particle circumference length data for individual particles are obtained by summing up all addition data of the same particle by comprising:

comparing means for obtaining a binary signal group for detecting particle portions by comparing the background correction signal group with a specific threshold, shrink/expand processing means for sampling the binary signal group in a specific period and obtaining a binary signal group by shrinking and expanding in every sampling in the binary signal group of a same particle, exclusive OR processing means for obtaining a binary signal group by calculating an exclusive OR of the binary signal group of the sampling and binary signal group of one preceding sampling, encoder means for obtaining continuous numbers of signals, exclusive OR binary signal group of the same particle, arithmetic means for calculating the square root data of the square sum of the signal numbers and moving extent data of the particles in one sampling period, and addition means for summing the square root data.

38. An apparatus for analyzing particles according to claim 33, further comprising means for obtaining the complexity data of individual particles by sampling the difference of adjacent signals of the background correction signal group, and summing up the magnitude of all the sampling difference signals of the same particle.

39. An apparatus for analyzing particles according to claim 33, wherein the characteristic parameters comprise light absorption information of the particle.

40. An apparatus for analyzing particles according to claim 33, wherein the characteristic parameters comprise morphological information of the particle.

41. An apparatus for analyzing particles according to claim 39, wherein one of the light absorption information comprises the light absorption quantity of the particle.

42. An apparatus for analyzing particles according to claim 39, wherein the light absorption information comprises the light absorption quantity and absorbance of the particle.

43. An apparatus for analyzing particles according to claim 42, wherein the absorbance is obtained by dividing the light absorption quantity by the particle area.

44. An apparatus for analyzing particles according to claim 40, wherein at least one of the morphological information is/are selected from a group consisting of particle area, the particle circumference length, the particle width, and complex quantity in the particle, and nucleus area.

45. An apparatus for analyzing particles according to claim 40, wherein at least one of the morphological information is/are selected from a group consisting of particle area, particle circumference length, particle width, and complex quantity in the particle, nucleus area, particle roundness, particle complexity, and nucleus area ratio.

46. An apparatus for analyzing particles according to claim 45, wherein the particle complexity is obtained by dividing the particle complex quantity by the particle area.

47. An apparatus for analyzing particles according to claim 45, wherein the particle roundness is obtained by dividing the particle area by the square of the particle circumference length.

48. An apparatus for analyzing particles according to claim 45, wherein the nucleus area ratio is obtained by dividing the nucleus area by the particle area.

* * * * *

UNITED STATES PATENT AND TRADEMARK OFFICE
CERTIFICATE OF CORRECTION

PATENT NO. : 5,457,526
DATED : October 10, 1995
INVENTOR(S) : Tokihiro Kosaka

It is certified that error appears in the above-indentified patent and that said Letters Patent is hereby corrected as shown below:

Claim 3, column 11, line 11, "the" (second occurrence) should be deleted.

Claim 13, column 12, line 5, "the" should be deleted.

Claim 19, column 12, line 61, "the" (second occurrence) should be deleted.

Claim 20, column 12, line 66, "the" (second occurrence) should be deleted.

Claim 21, column 13, line 11, "ad" should be "and".

Claim 25, column 13, line 39, "the" (third occurrence) should be deleted.

Claim 28, column 13, line 50, "the" (both occurrences) should be deleted.

Claim 44, column 16, line 9, "the" (both occurrences) should be deleted.

Signed and Sealed this

Twentieth Day of February, 1996

Attest:

BRUCE LEHMAN

*Attesting Officer*    *Commissioner of Patents and Trademarks*